US00PP28064P2

(12) United States Plant Patent
Berry

(10) Patent No.: US PP28,064 P2
(45) Date of Patent: May 30, 2017

(54) ***LAGERSTROEMIA* PLANT NAMED '11LI'**

(50) Latin Name: *Lagerstroemia indica*
Varietal Denomination: 11LI

(71) Applicant: Capstone Plants Inc., Grand Saline, TX (US)

(72) Inventor: James B Berry, Edgewood, TX (US)

(73) Assignee: CAPSTONE PLANTS INC., Grand Saline, TX (US)

( * ) Notice: Subject to any disclaimer, the term of this patent is extended or adjusted under 35 U.S.C. 154(b) by 72 days.

(21) Appl. No.: 14/756,350

(22) Filed: Sep. 1, 2015

(51) Int. Cl.
*A01H 5/02* (2006.01)

(52) U.S. Cl.
USPC ..... Plt./252

(58) Field of Classification Search
USPC ..... Plt./252
See application file for complete search history.

*Primary Examiner* — Anne Grunberg
(74) *Attorney, Agent, or Firm* — Penny J. Aguirre

(57) ABSTRACT

A new cultivar of *Lagerstroemia indica* plant named '11LI' that is characterized by its foliage that is silvery grey-green in color with red-purple veins, its flowers that are vivid magenta pink in color, its panicles that are long, wide and dense, and its resistance to powdery mildew and leaf spot.

2 Drawing Sheets

Botanical classification: *Lagerstroemia indica.*
Variety denomination: '11LI'.

BACKGROUND OF THE INVENTION

The present invention relates to a new and distinct cultivar of *Lagerstroemia indica*. The new *Lagerstroemia* will hereafter be referred to by its cultivar name, '11LI'. '11LI' is a new cultivar of crape myrtle grown for use as an ornamental landscape plant.

The new cultivar of *Lagerstroemia* is the result of a controlled breeding program conducted by the Inventor in Grande Saline, Tex. The objective of the breeding program is the develop new cultivars of crape myrtle that are pathogen resistant, have dark red pigmented foliage, have unique flower color, and that possess desirable production traits.

'11LI' originated as a seedling that arose from seeds sown from open pollination of *Lagerstroemia indica* 'Red Hot' (not patented) as the female parent in September of 2012. '11LI' was selected as a single unique plant in July of 2013 from amongst the resulting seedlings.

Asexual propagation of the new cultivar was first accomplished by the Inventor using semi mature softwood stem cuttings in August of 2013 in Grand Saline, Tex. Asexual propagation by semi mature softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish '11LI' as a unique cultivar of *Lagerstroemia.*

1. '11LI' exhibits foliage that is silvery grey-green in color with red-purple veins.
2. '11LI' exhibits flowers that are vivid magenta pink in color.

3. '11LI' exhibits panicles that are long, wide and dense.
4. '11LI' exhibits resistance to powdery mildew and leaf spot.

The female parent of '11LI', *Lagerstroemia indica* 'Red Hot', differs from '11LI' in having flowers that are red in color and in having a globular plant habit. '11LI' can also be compared to the *Lagerstroemia indica* cultivars 'Tuskegee' (not patented) and 'Whit V' (U.S. Plant Pat. No. 11,312). 'Tuskegee' is similar to '11LI' in having a similar flower color and plant habit. 'Tuskegee' differs from '11LI' in having mottled light grey bark, green foliage, less dense panicles and foliage that is susceptible to powdery mildew and leaf spot. 'Whit V' is similar to '11LI' in flower color and in having powdery mildew resistance. 'Whit V' differs from '11LI' in having a dwarfed and mounded growth habit and in having smaller green leaves.

BRIEF DESCRIPTION OF THE DRAWINGS

The accompanying colored photographs illustrate the overall appearance and distinct characteristics of the new *Lagerstroemia*. The photographs were taken of plants one year in age (from a liner) as grown outdoors in three-gallon containers in Grand Saline, Tex.

The photograph in FIG. 1 provides a side view of '11LI' in bloom.

Figure 1:
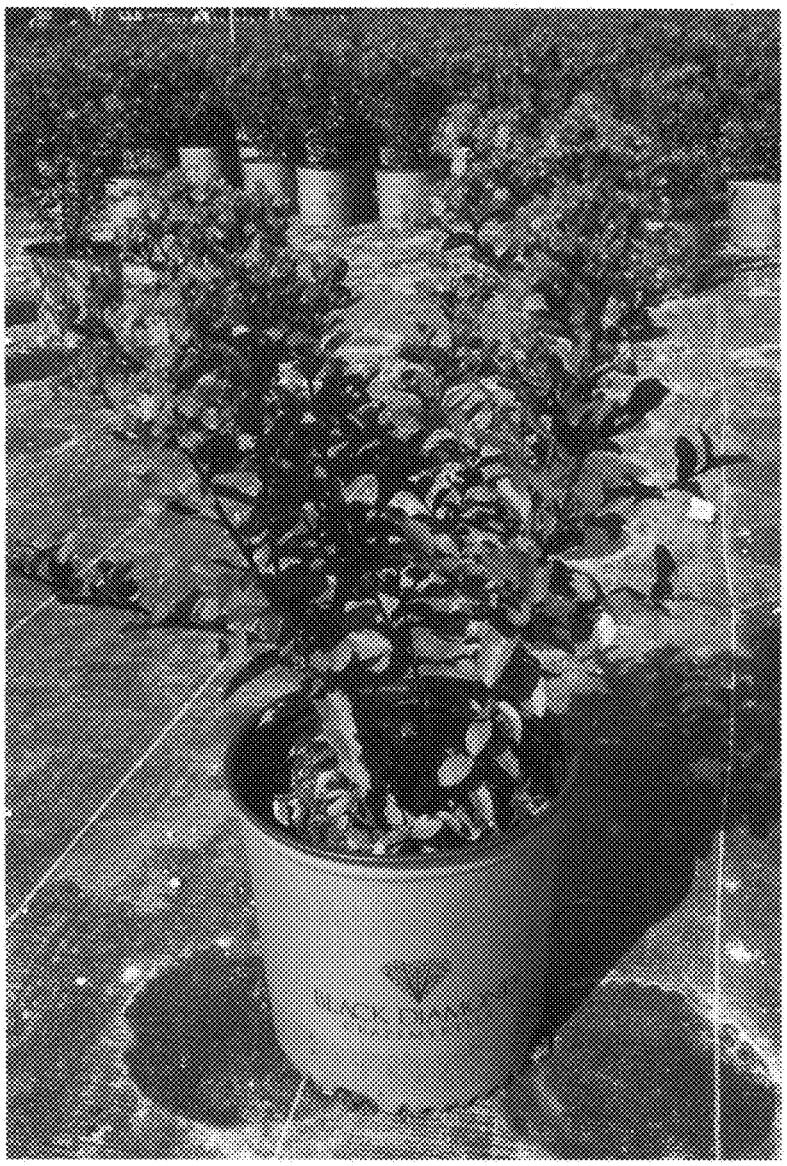
Figure 2:
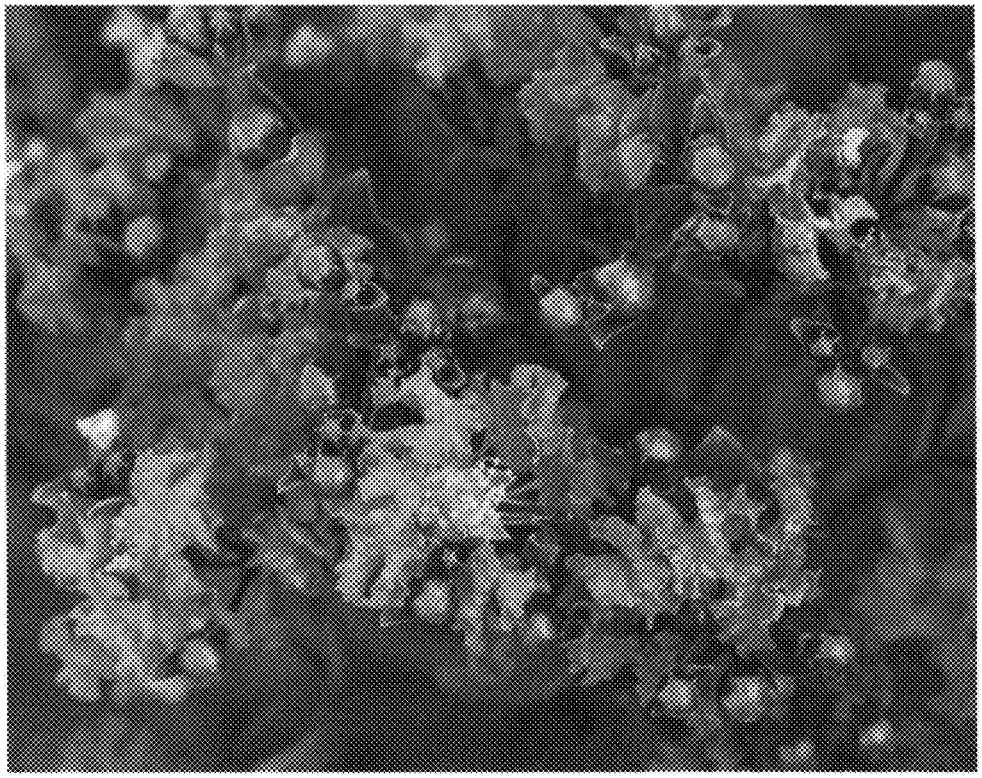

The photograph in FIG. 2 provides a close-up view of an inflorescence of '11LI'.

Figure 3:
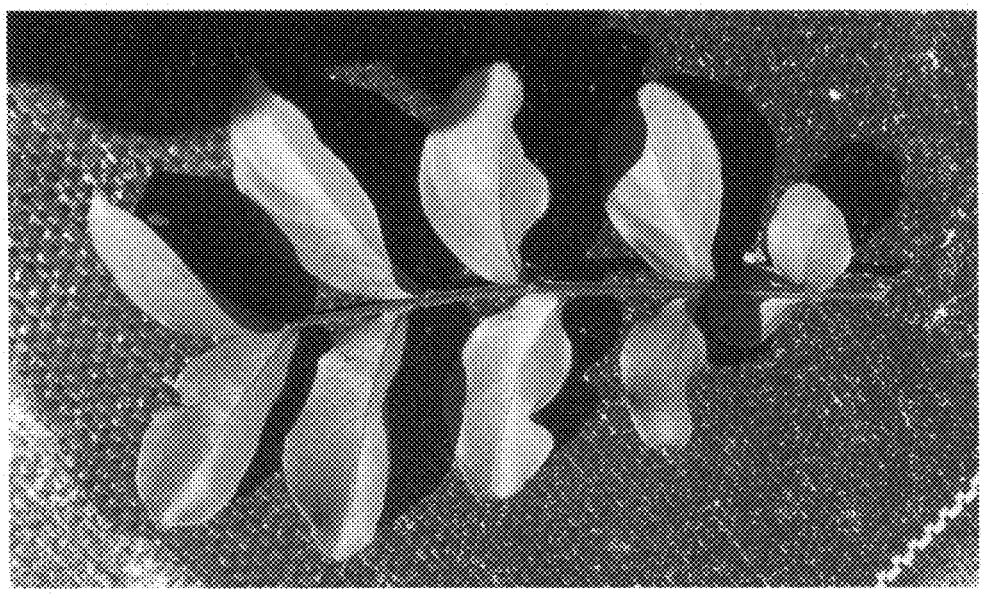

The photograph in FIG. 3 provides a close-up view of the foliage '11LI'.

The colors in the photographs are as close as possible with the digital photography techniques available, the color values cited in the detailed botanical description accurately describe the colors of the new *Lagerstroemia.*

DETAILED BOTANICAL DESCRIPTION

The following is a detailed description of plants one year in age (from a rooted cutting) as grown outdoors in one-gallon containers in Grand Saline, Tex. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Mid June to mid October in Texas.

*Plant type*.—Deciduous shrub.

*Plant habit*.—Upright.

*Height and spread*.—3 to 3.7 m in height and an average of 2.4 m in width as grown in the landscape.

*Hardiness*.—At least to U.S.D.A. Zone 6.

*Diseases and pests*.—Resistance to powdery mildew (*Erysiphe lagerstoemia*) and leaf spot (*Cercospora lythracearum*) has been observed.

*Root description*.—Fibrous and fine, N167C in color.

*Root development*.—An average of 2 weeks for root initiation and about 5 weeks to produce a young rooted plant.

*Propagation*.—Semi mature softwood stem cuttings.

*Growth rate*.—Moderately vigorous.

Stem description:

*Shape*.—Young stems; quadrangular with very small wings, mature stems; rounded.

*Stem color*.—Young and mature stems; a blend between 59A, 185A, and 200A, older stems; a blend between 164C, 165B, arid 200A to 200C.

*Stem size*.—Main stems; an average of 45 cm in length (after pruning) and 6 mm in diameter, secondary stems; up to 20 cm in length and 3 mm in width.

*Stem surface*.—Young and mature stems; glossy, smooth and rubbery, older stems; bark-like, dull, and rugose.

*Stem strength*.—Main stems; strong, secondary stems; moderately strong and flexible.

*Branching*.—Moderately branched, an average of 9 main branches and 3 lateral branches per main branch.

*Internode size*.—An average of 2 cm.

*Stem fragrance*.—Musty fragrance typical for *Lagerstroemia* detected when touched.

Foliage description:

*Leaf shape*.—Elliptic to oval.

*Leaf division*.—Simple.

*Leaf base*.—Rounded cuneate.

*Leaf apex*.—Acute to rounded.

*Leaf venation*.—Pinnate, color; upper surface mid-rib and main lateral veins; 183A, other veins match leaf surface, lower surface a blend between 159B and 184B, surface; moderately glossy and slightly covered with minute hairs <0.3 mm in length and NN155C in color.

*Leaf margins*.—Entire, very slightly undulate and hispidulous with minute hairs <0.3 mm in length that match leaf color.

*Leaf arrangement*.—Opposite.

*Leaf attachment*.—Petiolate.

*Leaf surface*.—Both surfaces; leathery and hispidulous with stiff hairs <0.3 mm in length that match the leaf color, upper surface dull, lower surface glossy.

*Leaf size*.—An average of 4 cm in length and 2.5 cm in width.

*Leaf quantity*.—An average of 26 (13 pairs) per main branch and 18 (9 pairs) per lateral branch.

*Leaf color*.—Young and mature leaves upper surface; a blend between NN137A, 147A, and 191A with thin line 187A at the margin, young and mature leaves lower surface; a blend between 138A and N199A.

*Leaf fragrance*.—Musty fragrance typical for Lagerstroemia detected when touched.

*Petioles*.—An average of 1 mm in length and width, upper and lower surfaces; 187A in color and glabrous.

Flower description:

*Inflorescence type*.—Terminal panicle.

*Lastingness of inflorescence*.—About one to two weeks.

*Inflorescence size*.—An average of 7 cm in height and 9 cm in width.

*Inflorescence number*.—An average of 1 to 2 per lateral stem.

*Flower number*.—An average of 10 flowers per inflorescence.

*Flower fragrance*.—Mild sweet scent.

*Flower buds*.—Globular in shape, an average of 7 mm in diameter depth, surface; glossy and striate with 6 main grooves slightly protruding from the surface, color; a blend of 176B and 183A.

*Flower aspect*.—Upright to slightly outwards.

*Flower type*.—Rotate.

*Flower size*.—An average of 1.5 cm in diameter and 7 mm in depth.

*Petals*.—An average of 6, ovate in shape, very curly with sinuate crenate margins, stalked base (attached between sepals), rounded apex, glabrous and dull upper and lower surfaces, an average of 7 mm in length and width (stalk portion is about 3 mm in length and >1 mm in width), color; upper and lower surfaces when opening and when fully open; a blend between N66A to N66B, 67A, and 71B, petal color does not fade.

*Calyx*.—Round in shape, an average of 7 mm in length and 5 mm in diameter.

*Sepals*.—An average of 6, 50% fused, elliptical in shape, acute apex spreading outwards, both surfaces glossy, an average of 6 mm in length and 3 mm in width, with free apex 3 mm in length and width, color; outer and inner surface when opening and when fully open; a mix of 156C, 183A to 183B and 186D.

*Peduncles*.—Moderately strong, an average of 2 cm in length and 2 mm in width, quadrangular in shape, a blend between 59A, 185A, and 200A in color, surface; dull and rubbery with translucent wings, held at an average angle of 60° to lateral stems.

*Pedicels*.—Moderately strong, an average of 1 cm in length and width, quadrangular in shape, surface; is dull and rubbery with translucent wings, a blend between 59A, 185A, and 200A in color, held at an average angle of 60° to the peduncle.

Reproductive organs:

*Stamens*.—An average of 30 clustered at the center and 6 evenly distributed around the outside, central stamens; anther; an average of 1 mm in length, dorsifixed, oblong to round in shape, 6A in color, filament; an average of 2 mm in length and 155B in color, outer stamens; anther; an average of 1.5 mm in length, dorsifixed, oblong in shape, a mix of N144A and 197C in color, filament; an average of 7 mm in length and 63C to 63D in color, pollen not observed.

*Pistils*.—An average of 1, an average of 5 mm in length, style; an average of 6 mm in length and 175B in color, stigma is club-shaped, 1 mm in length and 175A in color, ovary is globose in shape, about 2 mm in diameter, and 151A in color.

*Seed and fruit*.—None observed to date.

It is claimed:

1. A new and distinct cultivar of *Lagerstroemia* plant named '11LI' as herein illustrated and described.

* * * * *